United States Patent [19]
Kuwayama et al.

[11] Patent Number: 6,118,005
[45] Date of Patent: Sep. 12, 2000

[54] PROCESS FOR PREPARING HALOGENOPYRIDINE DERIVATIVES

[75] Inventors: Tomoya Kuwayama; Shinichi Inoue; Goro Asanuma; Manzo Shiono, all of Kurashiki, Japan

[73] Assignee: Kuraray Co., Ltd., Kurashiki, Japan

[21] Appl. No.: 09/068,115

[22] PCT Filed: Sep. 8, 1997

[86] PCT No.: PCT/JP97/03144

§ 371 Date: May 6, 1998

§ 102(e) Date: May 6, 1998

[87] PCT Pub. No.: WO98/11071

PCT Pub. Date: Mar. 19, 1998

[30] Foreign Application Priority Data

Sep. 10, 1996 [JP] Japan .................................. 8-238957

[51] Int. Cl.$^7$ ...................... C07D 213/61; C07D 213/62; C07D 213/71

[52] U.S. Cl. ............................. 546/345; 546/294

[58] Field of Search ............................................ 546/345

[56] References Cited

U.S. PATENT DOCUMENTS 5,529,976  6/1996  Kehne et al. ........................... 504/213

FOREIGN PATENT DOCUMENTS

| | | |
|---|---|---|
| 58-206564 | 12/1983 | Japan . |
| 1215387 | 12/1970 | United Kingdom . |
| WO96/26188 | 8/1996 | WIPO . |

OTHER PUBLICATIONS

Naomichi Furukawa, et al. "Selective IPSO–Substitution in Pyridine Ring and its Application for the Synthesis of Macrocycles Containing both OXA–and THIA–Bridges". Tetrahedron letters, vol. 24, No. 31, 1983, pp. 3243–3246. XP–002120840.

Naomichi Furukawa, et al. "IPSO–Substitution of a Sulphinyl or Sulphonyl Group Attached to Pyridine Rings and its Application for the Synthesis of Macrocycles". J. Chemical Society Perkin Trans. 1, No. 8, 1984, pp. 1839–1845. XP–002120841.

P. Van Broeck, et al. "Reaction of 3–$H$–Pyrano[3,4–$b$] INDOL–3–Ones and 3$h$–2–Benzopyran–3–Ones with Heterodienophiles: A Two–Step Synthesis for Some 9$h$–Pyrido [3,4–$b$]Indoles and Isoquinolines". Synthesis, 1992, pp. 473–476. XP–002120842.

Naomichi Furukawa, et al., "IPSO–Substitution Reactions of 2–and 4–Sulfonylpyridines with Grignard–Regents". Heterocycles, vol. 24, No. 12, 1986, pp. 3337–3340. XP–002120843.

Chem. Pharm. Bull., vol. 36, pp. 2244–2247 (1988).

Chemical Abstracts, vol. 100, 138966j (1984).

Chemical Abstracts, vol. 74, 87860e(1971).

Chemical Abstracts, vol. 125, 275662n(1996).

Kobunsbi Jikkengaku (Experiments in Polymer Science), vol. 2, Monomers I, p. 171(1971).

*The Chemistry of Alkenes* (Interscience Publishers), pp. 921–925 (1964).

J. Org. Chem., vol. 47, pp. 1451–1455(1982).

Ind. Eng. Chem., Fundam., vol. 13, pp. 168–179(1974).

*Organic Synthesis*, vol. 57, pp. 88–92(1977).

*Primary Examiner*—Alan L. Rotman
*Attorney, Agent, or Firm*—Oblon, Spivak, McClelland, Maier & Neustadt, P.C.

[57] ABSTRACT

A process for preparing halogenopyridine derivatives represented by the general formula (II)

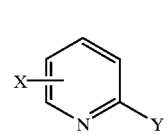

(II)

wherein X and Y each independently represent a halogen atom, comprises reacting a halogeno-2-sulfonylpyridine derivative represented by the general formula (I)

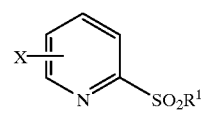

(I)

wherein X is as defined above and $R^1$ represents an alkyl group etc., with a halogenating agent.

The halogenopyridine derivatives can be produced with high purity and in a simple and easy and industrially advantageous manner.

3 Claims, No Drawings

PROCESS FOR PREPARING HALOGENOPYRIDINE DERIVATIVES

TECHNICAL FIELD

The present invention relates to a process for preparing halogenopyridine derivatives. The halogenopyridine derivatives produced in accordance with the present invention are useful as intermediates for the synthesis of medicinal and agrochemical compounds, for example as intermediates for the synthesis of lazabemide, which is under clinical development as an antiparkinsonian agent.

BACKGROUND ART

The so-far known processes for preparing halogenopyridine derivatives, for example 2,5-dichloropyridine, typically comprise reacting 3-chloropyridine-N-oxide with phosphorus oxychloride [cf. Chem. Pharm. Bull., Vol. 36, page 2244 (1988)], or chlorinating 2-chloropyridine (cf. Japanese Patent Application Laid-Open No. Sho 58-206564), or chlorinating 2-amino-5-chloropyridine (cf. Laid-open British Patent Specification 1,215,387).

However, the above-mentioned processes for preparing halogenopyridine derivatives cannot be said to be good processes for preparing halogenopyridine derivatives, since they have problems, for instance, the selectivity in the chlorination step is low, isomers which are difficult to separate are formed, and/or the raw materials are expensive.

On the other hand, a process for preparing pyridine derivatives by using a cyclization reaction is known. It comprises reacting a methyl-substituted butadienyl ester with a sulfonyl cyanide and then reacting the resulting methyl-substituted 2-sulfonylpyridine derivative with a halogenating agent to give the corresponding halogenomethyl-2-halogenopyridine (cf. Laid-open International Patent Application 96/26188). However, the cyclization reaction between a halogeno-1,3-butadienyl ester and a sulfonyl cyanide remains unknown and the halogenation of halogeno-2-sulfonylpyridine derivatives is also unknown.

It is known that when comparison is made between a methyl-substituted 1,3-butadiene (typically isoprene) and a halogen-substituted 1,3-butadiene (typically chloroprene), which are similar in structure and for which several cyclization reactions are known, the reactivity of chloroprene in the cyclization reactions is very low, namely 1/22 to 1/1100 of that of isoprene and chloroprene reacts slowly in spite of the fact that the difference in chemical structure therebetween is slight, namely the only difference is that the substituent is methyl or chlorine [cf. Kobunshi Jikkengaku (Experiments in Polymer Science), Vol. 2, Monomers I, page 171 (1971); The Chemistry of Alkenes (Interscience Publishers), page 921 (1964); J. Org. Chem., Vol. 47, page 1453 (1982); Ind. Eng. Chem., Fundam., Vol. 13, page 174 (1974)]. Furthermore, as regards the polymerization reaction predictable as a side reaction, it is known that chloroprene polymerizes more readily than isoprene [cf. Kobunshi Jikkengaku, Vol. 2, Monomers I, page 171 (1971)].

In spite of the above comparisons between isoprene and chloroprene, which make it very doubtful whether the use of a halogeno-1,3-butadienyl ester, instead of the corresponding methyl-substituted butadienyl ester, in the cyclization reaction known for the methyl-substituted butadienyl ester would allow the desired cyclization addition reaction to proceed with good efficiency, without leading to polymerization, the present inventors found that when a halogeno-1,3-butadienyl ester is reacted with a sulfonyl cyanide, the desired cyclization reaction proceeds with good efficiency. This finding has led to completion of the present invention.

The cyclization reaction between a methyl-substituted butadienyl ester and a sulfonyl cyanide is carried out batchwise, as described in the above-cited laid-open International Patent Application. The present inventors found that when the reaction is operated on a large scale, it becomes very difficult to control the reaction temperature, because such reaction involves marked heat generation while heating is required for initiating the reaction. While the same applies to the reaction between a halogeno-1,3-butadienyl ester and a sulfonyl cyanide, the present inventors found that it is possible to cause the desired cyclization addition reaction to proceed efficiently by carrying out the reaction while feeding the thermally unstable halogeno-1,3-butadienyl ester and sulfonyl cyanide to a heated reactor.

The primary object of the present invention is to provide an industrially advantageous process for preparing highly pure halogenopyridine derivatives in a simple and easy manner without using any expensive raw material.

DISCLOSURE OF THE INVENTION

The present invention relates to:

(1) A process for preparing halogenopyridine derivatives represented by the general formula (II)

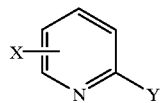

(II)

wherein X and Y each independently represents a halogen atom [hereafter abbreviated halogenopyridine derivatives (II)], which comprises reacting a halogeno-2-sulfonylpyridine represented by the general formula (I):

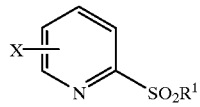

(I)

wherein X is as defined above and $R^1$ represents an alkyl group, a cycloalkyl group, an aryl group which may optionally be substituted, or an aralkyl group which may optionally be substituted [hereafter abbreviated halogeno-2-sulfonylpyridine derivative (I)], with a halogenating agent;

(2) A process for preparing halogenopyridine derivatives (II) which comprises reacting a halogeno-1,3-butadienyl ester represented by the general formula (III):

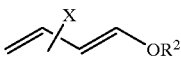

(III)

wherein X is as defined above and $R^2$ represents an acyl group [hereafter abbreviated halogeno-1,3-butadienyl ester (III)] with a sulfonyl cyanide represented by the general formula (IV):

$R^1SO_2CN$           (IV)

wherein $R^1$ is as defined above [hereafter abbreviated sulfonyl cyanide (IV)], and reacting the thus-obtained halogeno-2-sulfonylpyridine derivative (I) with a halogenating agent;

(3) A process as described above under (2) in which the reaction is carried out while continuously feeding the halogeno-1,3-butadienyl ester (III) and the sulfonyl cyanide (IV) to a reactor either simultaneously or alternately;

(4) A process for preparing a halogeno-2-sulfonylpyridine derivatives (I) which comprises reacting a halogeno-1,3-butadienyl ester (III) with a sulfonyl cyanide (IV); and (5) A process as described above under (4) in which the reaction is carried out while continuously feeding the halogeno-1,3-butadienyl ester (III) and the sulfonyl cyanide (IV) to a reactor either simultaneously or alternately.

BEST MODES FOR CARRYING OUT THE INVENTION

Referring to the above general formulas, the alkyl group represented by $R^1$ may be linear or branched and includes, for example, methyl, ethyl, propyl, isopropyl, butyl, sec-butyl, tert-butyl, pentyl, hexyl, octyl and decyl. The cycloalkyl group represented by $R^1$ includes, for example, cyclopropyl, cyclopentyl, cyclohexyl or cyclooctyl.

The aryl group represented by $R^1$ includes, for example, phenyl and naphthyl, and the aralkyl group represented by $R^1$ includes benzyl, phenetyl and the like. These aryl and aralkyl groups may have one or more substituents selected from among alkyl groups such as methyl, ethyl, propyl and tert-butyl, alkoxy groups such as methoxy, ethoxy and propoxy, halogen atoms such as fluorine, chlorine and bromine atoms, alkoxycarbonyl groups such as methoxycarbonyl, ethoxycarbonyl and propoxycarbonyl, cyano, nitro, etc.

As the acyl group represented by $R^2$ includes, for example, aliphatic acyl groups such as acetyl, propanoyl, butanoyl and pivaloyl, and aromatic acyl groups such as benzoyl.

As the halogen atoms represented by X and Y include fluorine, chlorine and bromine atoms.

First, the reaction between the halogeno-1,3-butadienyl ester (III) and the sulfonyl cyanide (IV) is described in detail.

Such reaction is carried out in the presence or absence of a polymerization inhibitor. The polymerization inhibitor to be used includes, for example, phenols such as 4-methoxyphenol and 2,6-di-tert-butyl-4-methylphenol; hydroquinones such as hydroquinone and di-tert-butylhydroquinone; naphthols such as 1-naphthol and 2-naphthol; catechols such as catechol and p-tert-butylcatechol; and amines such as phenothiazine, diphenylmine and 4-acetoxy-2,2,6,6-tetramethylpiperidine. The polymerization inhibitor is used preferably in an amount within the range of $1\times10^{-5}$ to 0.01 part by weight, more preferably in an amount within the range of $1\times10^{-4}$ to 0.001 part by weight, per part by weight of the halogeno-1,3-butadienyl ester (III).

The reaction can be conducted in the presence or absence of a solvent. The solvent to be used is not limited to any particular species unless it affects the reaction. As examples, there may be mentioned hydrocarbons such as benzene, toluene, xylene, cumene, hexane, heptane and octane; halogenated hydrocarbons such as dichloromethane, chloroform, carbon tetrachloride, 1,2-dichloroethane, 1,1,2,2-tetrachloroethane and chlorobenzene; ethers such as diethyl ether, diisopropyl ether, dibutyl ether, tetrahydrofuran, dioxane and dimethoxyethane; esters such as ethyl acetate and butyl acetate; nitriles such as acetonitrile and propionitrile; and amides such as dimethylformamide and N-methylpyrrolidone. The solvent is used preferably in an amount within the range of 0.5 to 20 parts by weight, more preferably within the range of 0.5 to 10 parts by weight, per part by weight of the sulfonyl cyanide (IV).

While the reaction may be carried out batchwise, it is preferred that the reaction, which is highly exothermic, may be carried out while continuously feeding the halogeno-1,3-butadienyl ester (III) and the sulfonyl cyanide (IV) to a reactor either simultaneously or alternately. The halogeno-1,3-butadienyl ester (III) is used in an amount preferably within the range of 0.1 to 100 moles, more preferably within the range of 0.5 to 2 moles, per mole of the sulfonyl cyanide (IV).

The reaction temperature is preferably within the range of 30° C. to 180° C., more preferably within the range of 40° C. to 150° C.

The thus-obtained halogeno-2-sulfonylpyridine derivative (I) can be isolated and purified from the reaction mixture by a conventional method. For instance, the reaction mixture is concentrated when necessary, the residue is cooled, and the product is separated and purified by recrystallization, distillation under reduced pressure, chromatography and/or some other technique. The halogeno-2-sulfonylpyridine derivative (I) obtained may be used in the next reaction step without isolation/purification.

Next, the reaction between the halogeno-sulfonylpyridine derivative (I) and a halogenating agent is described.

The halogenating agent may be any species capable of generating a halogen radical. From the reaction efficiency and cost viewpoints, chlorine, sulfuryl chloride, bromine, dibromodimethylhydantoin and the like are preferred. The halogenating agent may be added during the reaction either continuously or portionwise.

Such reaction can be carried out in the presence or absence of a radical initiator. Useful as the radical initiator are nitriles such as 2,2'-azobis(isobutyronitrile) [AIBN] and 1,1'-azobis(cyclohexanecarbonitrile); and peroxides such as benzoyl peroxide and acetyl peroxide, among others. The radical initiator may be added continuously or portionwise prior to the reaction and/or during the reaction. The amount of addition of the radical initiator is preferably within the range of 0.001 to 3.0 equivalents, more perferably within the range of 0.01 to 0.3 equivalent. It is also possible to induce radical generation by light irradiation.

The reaction can be carried out in the presence or absence of a solvent, but preferably in a solvent. The solvent is not limited to any particular species unless it affects the reaction. For instance, acetonitrle, carbon disulfide, tetrachloroethane, chlorobenzene, chloroform, carbon tetrachloride and the like may be used.

The reaction temperature is preferably within the range of 20° C. to 120° C., more preferably within the range of 60° C. to 100° C. While the reaction time depends on the reaction conditions, a reaction period of up to 8 hours is generally appropriate.

The thus-obtained halogenopyridine derivative (II) can be isolated and purified from the reaction mixture by a conventional method. For example, the reaction mixture is washed with an aqueous solution of sodium thiosulfate, an aqueous solution of sodium bicarbonate, an aqueous solution of sodium chloride, or the like, and then concentrated, and the residue is subjected to separation/purification by recrystallization, distillation, sublimation, chromatography and/or some other technique.

The starting halogeno-1,3-butadienyl ester (III) can be obtained, for example by reacting the corresponding halogeno-2-butenal with the corresponding carboxylic acid anhydride in the presence of the corresponding sodium carboxylate. The halogeno-2-butenal can be synthesized, for example by subjecting crotonaldehyde to addition of the corresponding halogen, followed by hydrogen halide elimination. The sulfonyl cyanide (IV) can be prepared from the corresponding sodium sulfinate or sulfonyl chloride by a known method [cf. Organic Syntheses, Vol. 57, page 88 (1977)].

The following examples illustrate the present invention in further detail. They are, however, by no means limitative of the scope of the present invention.

EXAMPLE 1

Synthesis of 2-benzenesulfonyl-5-chloropyridine

Toluene (60 ml) was heated to 100° C. Thereto was added dropwise a solution of 39.6 g of 2-chloro-1,3-butadienyl acetate and 30.0 g of benzenesulfonyl cyanide (purity:82%) in 60 ml of toluene over 30 minutes. The reaction mixture was stirred at 100° C. for 7 hours and then concentrated under reduced pressure. The crystals obtained were washed with 150 ml of toluene which was cooled to 0° C. and dried under reduced pressure using a vacuum pump to give 31.9 g of 2-benzenesulfonyl-5-chloropyridine (yield 86%).

$^1$H-NMR spectrum (270 MHz) δ (ppm) 7.50–7.68 (m, 4H), 7.89 (dd, J=2.3 Hz, 8.0 Hz, 1H), 8.02–8.09 (m, 1H), 8.16 (d, J=8.0 Hz, 1H), 8.60 (d, J=2.3 Hz, 1H)

EXAMPLE 2

Synthesis of 2,5-dichloropyridine

2-Benzenesulfonyl-5-chloropyridine (5 g) was dissolved in 50 ml of acetonirile, 650 mg of AIBN was added thereto, and chlorine gas was introduced into the mixture at a rate of 10 ml/minute for 1.5 hours and then at a rate of 20 ml/minute for 3.5 hours, with heating under reflux. The excess chlorine was removed from the resulting reaction mixture by bubbling with nitrogen and then concentrated under reduced pressure, the residue was dissolved in ethyl acetate, and the solution was washed with an aqueous solution of sodium bicarbonate and an aqueous solution of sodium chloride. The organic layer was dried and then concentrated under reduced pressure.

Purification by silica gel column chromatography gave 2.34 g of 2,5-dichloropyridine (yield 80%).

EXAMPLE 3

Synthesis of 2-benzenesulfonyl-5-bromopyridine

The procedure of Example 1 was followed except that 51.6 g of 2-bromo-1,3-butadienyl acetate was used instead of 39.6 g of 2-chloro-1,3-butadienyl acetate. After separation and purification, 36.8 g of 2-benzenesulfonyl-5-bromopyridine was obtained (yield 84%).

$^1$H-NMR spectrum (270 MHz) 6 (ppm) 7.55 (dd, J=1.5 Hz, 7.4 Hz, 1H), 7.51–7.67 (m, 2H), 8.05 (d, J=7.4 Hz, 1H), 8.03–8.08 (m, 3H), 8.71 (d, J=1.5 Hz, 1H)

EXAMPLE 4

Synthesis of 2-benzenesulfonyl-5-chloropyridine

A tubular reactor (capacity:1 ml, voidage:100%) was heated to 100° C. To the reactor was fed a toluene solution of 2-chloro-1,3-butadienyl acetate (44 volume percent, 3.0 moles/L) at a flow rate of 6.4 ml/hour, and benzenesulfonyl cyanide (79 volume percent, 4.69 moles/L) at a flow rate of 4.1 ml/minute for 1 hour (residence time 5.7 minutes). The effluent was ice-cooled for recrystallization, the crystals were collected by filtration, washed with cold toluene and dried under reduced pressure using a vacuum pump to give 4.39 g of 2-benzenesulfonyl-5-chloropyridine (yield 90.1%).

Industrial Applicability

The present invention provides a process for preparing high-purity halogenopyridine derivatives in a simple and easy and industrially advantageous manner. The halogenopyridine derivatives produced in accordance with the present invention are useful as intermediates for the synthesis of medicinal and agrochemical compounds, for example as intermediates for the synthesis of lazabemide, which is under clinical development as an antiparkinsonian agent.

What is claimed is:

1. A process for preparing halogenopyridine derivatives represented by the general formula (II)

wherein X and Y each independently represent a halogen atom, which comprises reacting a halogeno-2-sulfonylpyridine derivative represented by the general formula (I)

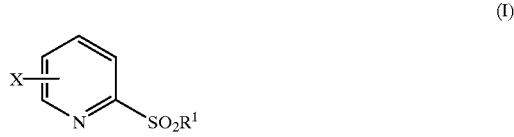

wherein X is as defined above and $R^1$ represents an alkyl group, a cycloalkyl group, an aryl group which may optionally be substituted, or an aralkyl group which may optionally be substituted, with a halogenating agent.

2. A process for preparing halogenopyridine derivatives represented by the general formula (II)

wherein X and Y each independently represent a halogen atom, which comprises reacting a halogeno-1,3-butadienyl ester represented by the general formula (III)

wherein X is as defined above and $R^2$ represents an acyl group, with a sulfonyl cyanide represented by the general formula (IV)

wherein $R^1$ represents an alkyl group, a cycloalkyl group, an aryl group which may optionally be substituted, or an aralkyl group which may optionally be substituted, and reacting the thus-obtained halogeno-2-sulfonylpyridine derivative represented by the general formula (I)

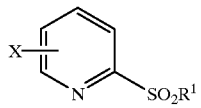
(I)

wherein X and $R^1$ are as defined above with a halogenating agent.

3. A process as claimed in claim 2, wherein a reaction is carried out while continuously feeding a halogeno-1,3-butadienyl ester represented by the general formula (III)

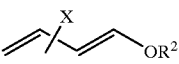
(III)

wherein X represents a halogen atom and $R^2$ represents an acyl group and a sulfonyl cyanide represented by the general formula (IV)

$R^1SO_2CN$ (IV)

wherein $R^1$ represents an alkyl group, a cycloalkyl group, an aryl group which may optionally be substituted, or an aralkyl group which may optionally be substituted, to a reactor either simultaneously or alternately.

* * * * *